United States Patent [19]

Messens et al.

[11] Patent Number: 4,463,316
[45] Date of Patent: Jul. 31, 1984

[54] METHOD AND APPARATUS FOR DETERMINING THE DYNAMIC SURFACE POTENTIAL OF A SOLUTION

[75] Inventors: Joseph L. Messens, Brasschaat; Frans J. Villé, Edegem; Roland F. Beels, Linkebeek, all of Belgium

[73] Assignee: AGFA-Gevaert N.V., Mortsel, Belgium

[21] Appl. No.: 395,914

[22] Filed: Jul. 7, 1982

[30] Foreign Application Priority Data

Jul. 10, 1981 [GB] United Kingdom ............... 8121366

[51] Int. Cl.³ ............................................. G01N 27/02
[52] U.S. Cl. .................................. 324/447; 324/449; 324/450; 324/453; 324/457
[58] Field of Search ............... 324/447, 449, 450, 452, 324/453, 457, 458; 204/1 T, 212, 222, 400, 409, 411, 412; 73/53, 61 R

[56] References Cited

U.S. PATENT DOCUMENTS

| | | | |
|---|---|---|---|
| 3,365,376 | 1/1968 | Weyland | 324/447 |
| 3,790,464 | 2/1974 | Greaves | 204/212 |
| 4,267,511 | 5/1981 | Suzuki et al. | 324/458 |

Primary Examiner—Michael J. Tokar
Assistant Examiner—Kevin D. O'Shea
Attorney, Agent, or Firm—William J. Daniel

[57] ABSTRACT

Method and apparatus of determining the dynamic surface potential of a solution, wherein a steady stream of the solution is formed, and the surface potential at a free surface of the stream of solution is measured by means of a rotary electrode that rotates in close vicinity of, but separated from, the free surface of the solution, and is mounted within an electrically grounded chamber.

10 Claims, 6 Drawing Figures

METHOD AND APPARATUS FOR DETERMINING THE DYNAMIC SURFACE POTENTIAL OF A SOLUTION

This invention relates to a method of assessing the dynamic surface potential of a solution, wherein the solution is formed into a steady stream having a free surface, and the difference between the surface potential of a reference electrode and the surface potential of the solution at a position along the stream is determined and used as a measure of said dynamic surface potential. The invention also relates to apparatus for use in carrying out such a method.

An assessment of the dynamic surface potential of a solution can be used as a measure of the adsorption of solute molecules upon a freshly formed surface of the solution, and as a measure of surface tension. The relationship between surface potential and solute adsorption can be determined by means of the Gibbs adsorption isotherm or from an assumed equation of state. The relationship between surface potential and surface tension can be found by measurements of both quantities upon solutions at equilibrium.

Techniques whereby the dynamic surface potential of a solution as a function of solution surface ages from approximately 0.001 to 1.0 second are known (see the article entitled "A New Technique for the Determination of Dynamic Surface Tensions" by A. M. Posner and A. E. Alexander in Transactions of the Faraday Soceity, 1949, 45, pp 651–661). One of the known methods utilises a so-called channel apparatus and is suitable for determining surface potentials for surface ages between approximately 0.02 and 1.0 second. In the other known method the surface potential measurements are made upon a free jet of the solution. By that method surface potentials can be determined for surface ages between approximately 0.001 and 0.01 second. In both of the known methods the potential measurements are made by ionizing the air space between the surface of the solution stream and the measuring electrode and using a high impedance electrometer as an indicating device.

In the foregoing known methods the optimum spacing between the liquid surface and the electrode is approximately 1 cm. If a significantly smaller spacing is used, as would be desirable for increasing the accurate localisation of the measurement at a predetermined position along the liquid stream, the measurement of potentials is liable to be disturbed by condensation of liquid vapours on the electrode. Another disadvantage of the known methods is that stray ionization of the radioactive emitter is liable to influence the surface potential readings because of contact of the ionized air with materials other than the liquid and the measuring electrode. Moreover safety measures are necessary, and the α-emitter, usually Polonium or AM 241, deteriorates with time.

It is an object of the present invention to provide a method in which the measuring electrode can be located much closer to the surface of the liquid stream while at the same time avoiding or reducing measurement disturbances caused by vapour condensation, and in which ionization of the liquid/electrode interspace is unnecessary.

According to the present invention, a method of assessing the dynamic surface potential of a solution, wherein the solution is formed into a steady stream having a free surface, and the difference between the surface potential of an electrode and the surface potential of the solution at a position along the stream is determined and used as a measure of dynamic surface potential is characterised thereby that a rotating electrode is used, the elctrode being formed and arranged so that at least one electrically conductive peripheral surface portion thereof moves repeatedly in a direction across the path of the liquid stream thereby causing a succession of potential difference signals to be yielded, and in that the dynamic surface potential of the solution is assessed from those signals.

As in the prior art methods hereinbefore referred to, the potential difference measurements are a measure of the dynamic surface potential of the solution, but not an absolute evaluation of it. For many purposes, e.g. in the determination of the wetting properties of solutions preparatory to their use as coating materials for coating various substrates, absolute measurement of surface potential is not a frequent requirement. It is often sufficient for skilled workers to make comparisons between the potential difference measurements relating to different solutions, e.g. solutions containing different wetting agents or containing a wetting agent in different concentrations.

The method according to the invention affords the advantage that the measuring distance, i.e. the spacing between the liquid stream surface and the surface of the electrode can be much smaller than in the prior art methods without the occurrence of difficult problems caused by vapour condensation on the electrode. This is because the or each electrically conductive surface portion of the electrode sweeps into and out of the environment in the immediate vicinity of the liquid stream during each revolution of the electrode, and for the greater part of each revolution the or each said conductive surface portion is in an environment which is free or can easily be freed of vapours. In extreme situations, for instance when testing certain solutions at elevated temperatures, some vapours may reach regions of the electrode environment which are remote from the liquid stream but vapours in those regions can quite easily be removed by ventilating the electrode environment.

It is not essential for the path of the electrode periphery to cross the liquid stream in a direction substantially normal to the direction of the stream at the measuring position but that arrangement is preferred. The self-cleaning effect on the electrode tends to become less if the said electrode periphery travels obliquely across the stream, particularly at angles which depart appreciably from a right angle.

In preferred embodiments of the invention, the measuring distance, i.e. the distance between the surface of the solution stream and the electrode at its closest position to the stream, is less than 1 mm. At such a distance a very high measuring accuracy or sensitivity is possible. In the most preferred embodiments, the said distance is smaller than 0.5 mm.

It is preferred for the stream of solution to be in the form of a jet, because the velocity of the stream surface can then be more easily made substantially equal to that of the internal part of the stream, and the surface age at any point along the stream can be accurately calculated. Moreover the absence of mechanical support for the stream at the point of measurement is helpful in promoting measurement accuracy. It is particularly satisfactory for the trajectory of the jet to be substantially horizontal at the measuring position. It is preferably for the electrode to be rotated about a horizontal axis which is in or substantially in the same horizontal plane as the axis of the jet at the measuring position. In these circumstances, slight deviations of the jet trajectory in the vertical plane can occur without substantially affecting the measuring distance between the jet and the electrode and that distance can be set very small in order to achieve maximum sensitivity while at the same time reducing to a minimum the risk of contact between the jet and the electrode.

The invention includes apparatus for use in assessing the dynamic surface potential of a solution, comprising means for producing a steady stream of the solution to be tested, said stream having a free surface, an electrode located so that in operation of the apparatus such electrode is adjacent said free surface at a certain position along such stream, and means for determining the difference between the surface potential of the solution at said position and the surface potential of said electrode, characterised in that said electrode has a plurality of electrically conductive surface portions angularly spaced around an axis and is rotatable about such axis to cause said surface portions to follow a path directed across said stream thereby to yield, for the determination of said potential difference, a plurality of potential difference signals during each revolution of the electrode.

Such apparatus for carrying out a method as hereinbefore defined affords the advantage, in addition to the self-cleaning effect of the electrode rotation, that the frequency of the measuring signals is favourably influenced by the presence of a plurality of electrode poles, and the response time of the apparatus can be relatively short. It is desirable for the mesuring frequency to be such that the influence of inducted foreign electrical signals on the measurements is negligible. A measuring frequency of 75 Hz has been found very effective for filtering out parasitic signals at 50 Hz deriving from a mains supply.

The rotary electrode may be in the form of a metal wheel with an interrupted peripheral surface, e.g. having a form akin to that of a gear wheel or sprocket wheel. An electrode of such a form is easy to manufacture with the required high precision.

The rotary electrode is preferably mounted in an electrical shield chamber, and drivable at an independently controllable speed. It is preferable for the electrode to be driven via an indirect coupling, e.g. via a magnetic coupling, the power source being located outside said chamber. By these measures, the influence of electrical disturbance and mechanical vibrations can be considerably reduced.

As already indicated it is preferable for the steady stream on which the measurements are performed to be in the form of a jet. Preferably therefore the apparatus comprises means for producing such a jet. This means may comprise a capillary tube having a restriction near its liquid discharge end for promoting the formation of a jet which is steady and shock-free over a wide range of trajectory distances from such tube.

The apparatus and method according to the present invention have in the first place been devised for determining the dynamic surface potential of liquid photographic coating compositions that are to be coated on a support. Photographic coating compositions typically consist of aqueous solutions or dispersions of hydrophilic colloids with other materials dissolved or dispersed therein. The coating of these compositions on a support in order to manufacture photographic elements is an extremely difficult art requiring accurate control. A particularly influential factor is the wetting properties of the coating composition. As a matter of fact, insufficient wetting properties limit the maximum possible coating speed and/or are the cause of local defects that require careful detection, mostly in darkroom conditions, in order to maintain an acceptable quality level.

The problem is aggravated in modern photographic multilayer coating methods, such as bead coating and curtain coating, by the fact that at least two more layers of different coating compositions are first applied onto each other, and then as one integral composite layer onto the support. The wetting problem is thus no longer limited to the wetting at a liquid/solid interface, namely the lowermost layer of the composite layer that enters in contact with the support, or with an already dried primer or substrate layer on the support, but it extends also to the wetting contact at the liquid/liquid interfaces of the different layers. Conventional measuring methods for determining the wetting properties of a solution on the basis of its surface tension, may give useless results in practice because it may occur that two distinct liquids may each properly wet a support, but may tend to repel each other. This is because a measurement of the surface tension in itself does not give any information about the type of wetting agent, such as anionic, non-ionic, etc.

For these reasons, the examples in the following description deal in particular with the adsorption upon a freshly formed surface of solute agents that are used in the manufacturing of photographic materials.

It will be understood, however, that the method and apparatus of the invention are of equal value for the study of the kinetics of wetting in other fields, for instance in the search for efficient wetting agents to promote the rapid and even penetration of water into textile fibers, yarns and fabrics.

The invention is described hereinafter by way of example with reference to the accompanying drawings wherein.

Figure 1:
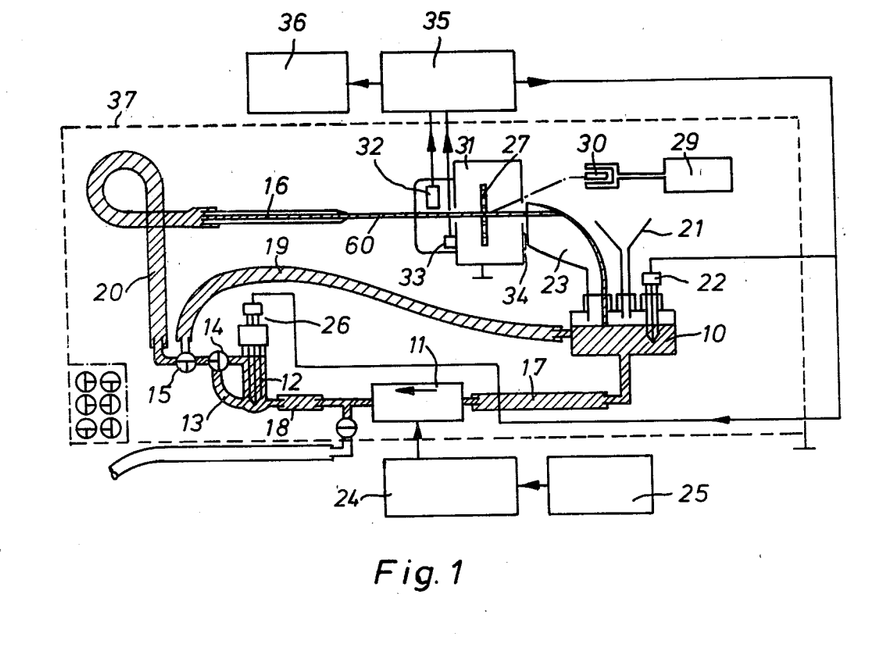
FIG. 1 is a diagrammatic representation of one embodiment of a apparatus according to the invention.

Referring to FIG. 1, the liquid circuit of the apparatus comprises a vessel 10, a pump 11, a small closed vessel 12 with a by-pass 13, two three-way valves 14 and 15, and a jet-forming rigid tube in the form of a capillary glass tube 16. The different elements are interconnected by flexible plastic tubes such as 17, 18, 19 and 20. Means may be provided for maintaining the liquid at a generally constant temperature. In a suitable form, this may comprise a double-walled construction of the vessels 10 and 12, and a double-walled portion of the length of the conduit 19, and heated water that is circulated through said double walls.

The vessel 10 may be a glass vessel having a loosely fitting cover through which extends a filling funnel 21, a standard electrode 22, for instance a calomel electrode for establishing galvanic contact with the liquid, and a collector tube with a widened inlet 23 for the jet liquid.

The pump 11 may be a membrane type positive displacement pump that is driven by an electromagnetic vibrator, whereby a very constant rate of flow may be obtained. Minor pump pulsations in the liquid stream are damped by the flexible plastic tubes. The rate of flow of the pump may be set by means of an adjustable transformer 24 that is connected to the mains supply via a voltage stabiliser 25.

The vessel 12 serves for effecting deaeration of the liquid supplementary to that which spontaneously occurs in the vessel 10. A second standard electrode 26 of the same type as the first electrode 22, is in galvanic contact with the liquid in the vessel 12, and is fluid-tightly fitted in that vessel. The first and second electrodes are connected in parallel so that the impedance of the electric coupling is about halved.

The purpose of the two three-way valves 14 and 15 is as follows. In a first position of the two valves that is illustrated by the first of the three lines of symbols in the insert bounded by drain lines in the left-lower corner of FIG. 1, the liquid of the vessel 10 is circulated through the vessel 12 and the branch 13, and through the tube 19 returned to the vessel 10. This is the valve position for bringing the apparatus into the stand-by mode. In the second position of the valves, that is illustrated by the second line of the insert, the liquid flows through the by-pass 13 and then to the conduit 19. During this circulation of the liquid, air bubbles that have not been removed in the vessel 10, are separated in the vessel 12 and will accumulate near the topside of said vessel. This separation is based on the fact that air bubbles escape upwardly during the cross-over of the liquid from the inlet of the vessel 12 towards the by-pass 13. In the third position of the valves, which is the measuring position, illustrated by the third line, the liquid flowing via by-pass 13 is directed to the jet forming tube 16. The valves may be hand-controlled or automatically controlled.

The arrangement for measuring the dynamic surface potential of the jet at a determined locus therealong comprises a rotary electrode 27 and motor means 29 for rotating the electrode. The coupling between the motor and the electrode may occur through a magnetic coupling such as 30. The electrode 27 is mounted within an electrically shielded measuring chamber, such as the grounded chamber 31. This chamber houses also a DC pre-amplifier 32 for amplifying the measurement signal of the electrode 27, and a transducer 33 that transduces the movements of the teeth of the wheel 27 as will be described further. The transducer may be a photocell, preferably an IR-sensitive cell, that is illuminated by a source of IR radiation 34, the rotary electrode intercepting periodically the IR radiation upon its rotation.

The apparatus finally comprises an electronic circuit 35 for the processing of the output signals of the pre-amplifier 32 and of the transducer 33 thereby to produce a compensation voltage such that the algebraic sum $V_{spd}+V_{se}+V_c=0$, wherein $V_{spd}$ is the difference between the dynamic surface potential of the solution and the surface potential of the measuring electrode, $V_{se}$ is the potential of the standard electrode with respect to the liquid, and $V_c$ is the compensation voltage. The measurement thus occurs according to the so-called compensation method, whereby the current through the circuit is zero at equilibrium. The voltage $V_c$ may be fed to a recorder 36.

The dashed line 37 represents the electric screening of the apparatus. This screening may have an electric conductivity that is far less than the conductivity of the chamber 31, and it has been shown that a metal housing with panels of electrically conductive glass with a conductivity of about $10^{-5}$ ohms$^{-1}$ offered excellent results, both for the electric screening of the apparatus and for the operability thereof.

Figure 2:
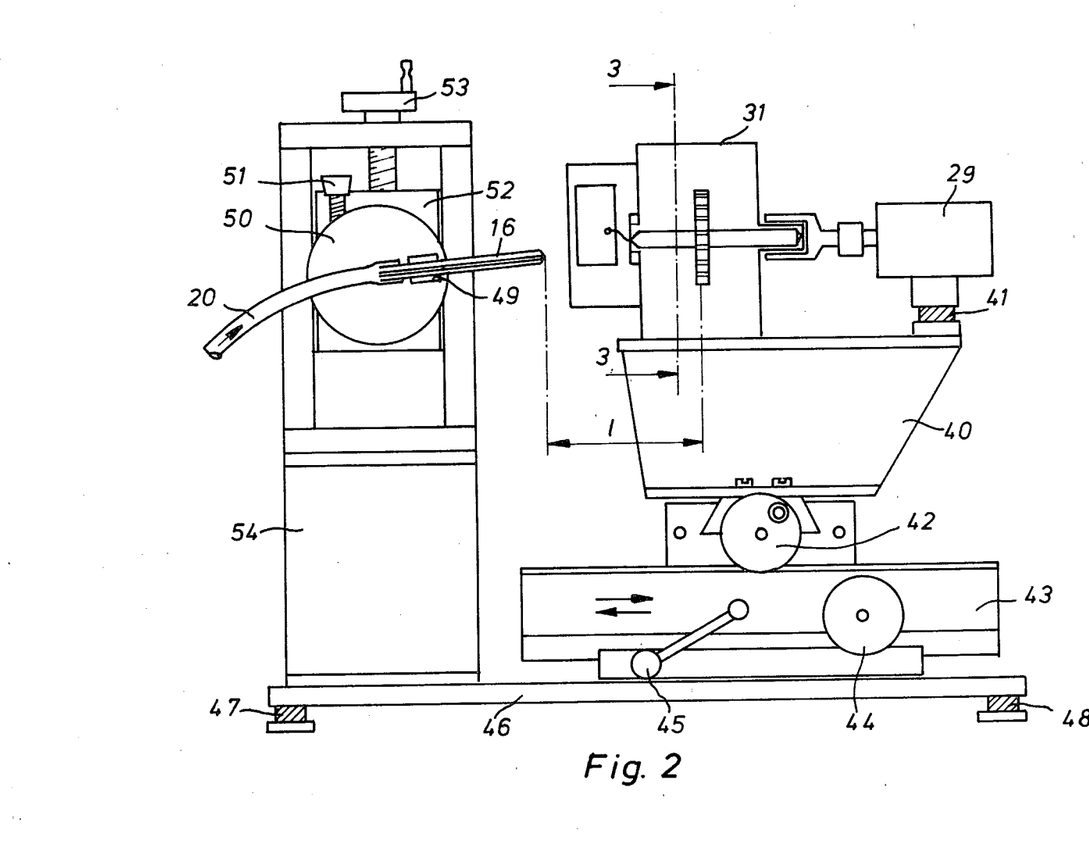
FIG. 2 is a front view of the apparatus according to FIG. 1, illustrating the different mechanical adjustments.

Details of the mechanical construction of the apparatus are now set forth with reference to FIGS. 2, 3 and 4. Referring to FIG. 2 which is a front view of the apparatus illustrating the various mechanically adjustable members, the measuring chamber 31 is rigidly mounted on a heavy solid support 40 of metal, concrete or the like. The motor 29 is mounted on that support through vibration dampers such as 41. The support 40 is movable in a direction normal to the plane of the drawing by means of a screw motion slide assembly 42. The base of the assembly 42 is fitted on a translating roll-table 43 that may be arranged for rapid displacement in a direction parallel with the plane of the drawing, for instance under the control of a rack and pinion mechanism actuated by a knob 44 and lockable by a lever 45. The roll-table 43 is fitted on a sturdy base plate 46 that is provided with resilient supports such as 47 and 48 that may also be arranged for the levelling of the apparatus. The capillary tube 16 is removably clamped in a holder 49 that is fitted to a rotary table 50. Rotation of the table about a horizontal axis by means of a knob 51 permits the inclination of the tube to be set. The height level of the tube may be set by means of the screw slide assembly 52 which is vertically displaceable by means of a handle 53. The adjustment assemblies for the capillary tube are mounted on a support 54 that is fitted to the base plate 46.

The capillary tube 16 is a glass tube with a length of 130 mm, an outer diameter of 8 mm and an inner diameter of 2 mm. The tube was cut from a standard length of tube and its end faces were treated to remove any sharp edges. It was found that a restriction of the diameter of the tube at the outlet end by at least 15%, was extremely useful for the realization of a steady, shockfree liquid jet over a wide range of measuring distances. In the present example, the tube outlet was restricted by 25% so that the actual outlet diameter was 1.5 mm.

The elements illustrated in FIG. 2 are mounted together with the components of the liquid circuit in a rectangular housing as represented by the dashed line 37 illustrated in FIG. 1. The measuring chamber is represented in more detail in FIG. 3 that is a transverse vertical section on line 3—3 of FIG. 2, and in FIG. 4 that is a longitudinal vertical section on line 4—4 of FIG. 3.

The measuring chamber 31 is constructed of a section of an aluminium tube to which circular end walls 55 and 56 have been welded. After welding such end walls in place the resulting chamber has been cut chordally vertically to separate a cover 57 which is then hingedly connected to the remaining body portion of the chamber at 58. The cover 57 can be secured in the illustrated closed position by locking means, not shown. A circular opening 59 is formed in the end wall 56 and a corresponding opening, co-axial with opening 59 is formed in the opposed end wall 55. These openings permit the free passage of the liquid jet 60 through the chamber. Two further openings such as 61 and 62 in the end walls 55 and 56 provide an optical path way 63 from the IR emitter 34 towards the photocell 33.

Figure 3:
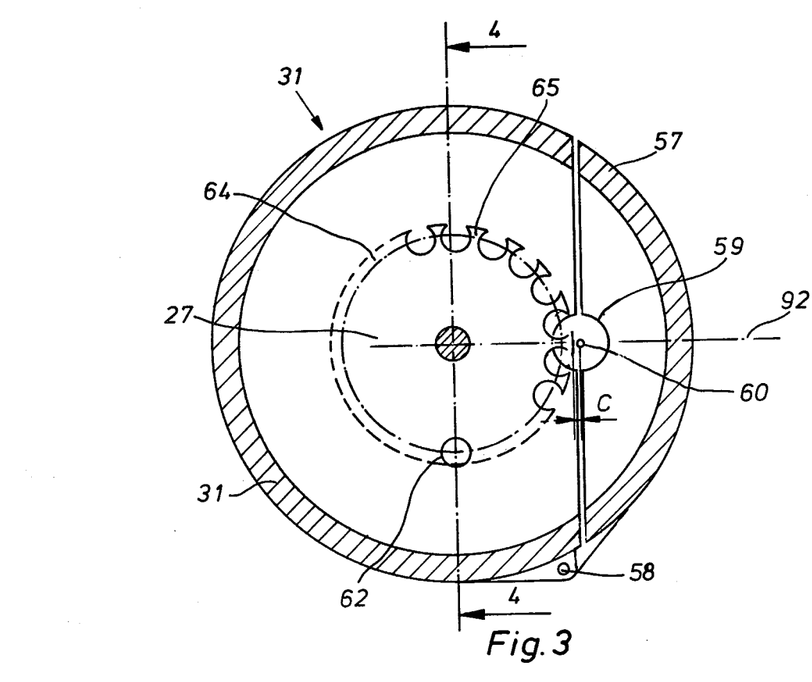
FIG. 3 is a transverse vertical section on line 3—3 of FIG. 2, through the measuring chamber.
Figure 4:
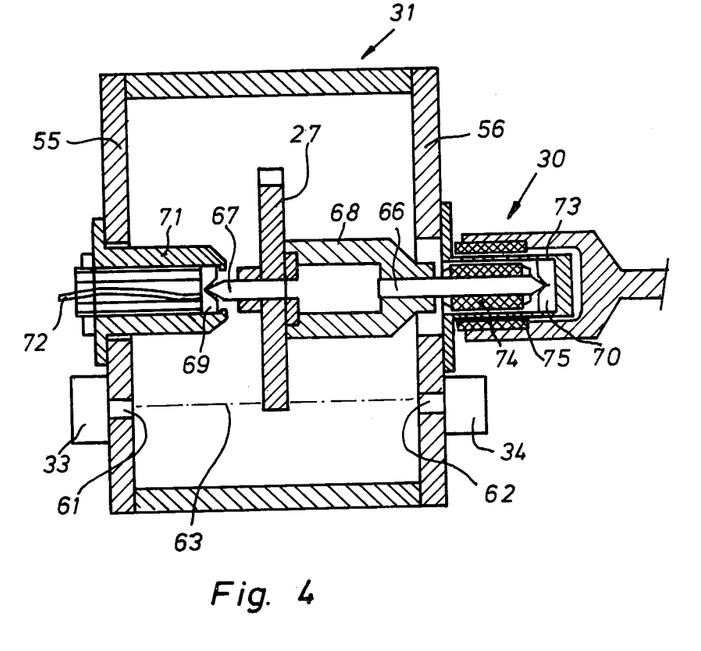
FIG. 4 is a longitudinal vertical section through the measuring chamber on line 4—4 of FIG. 3.

The measuring wheel 27 has a form as seen in FIG. 3. The wheel is made of stainless steel, and has been machined by providing a disc with a plurality of adjacent bores centred on a pitch circle 64, and by then turning off the wheel to the illustrated outer diameter thereby cutting across the bores and forming the teeth 65.

The wheel 27 has two shafts 66 and 67, the shaft 66 being fitted to the wheel by means of an electrically insulating mounting 68. The wheel is rotatably journalled in metal V-notch bearings 69 and 70. The bearing 69 is electrically insulated by means of the plastic mounting 71, and is connected by the insulated conductor 72 to the input of the pre-amplifier 32. The bearing 70 is mounted in a bushing 73 of diamagnetic material, such as brass, that is fitted to the wall 56 of the chamber 31.

The magnetic coupling 30 of the shaft 66 with the driving motor comprises the concentric magnetic rings 74 and 75 that each have a plurality of corresponding magnetic poles. This coupling efficiently eliminates vibrations caused by the motor 29.

Figure 5:
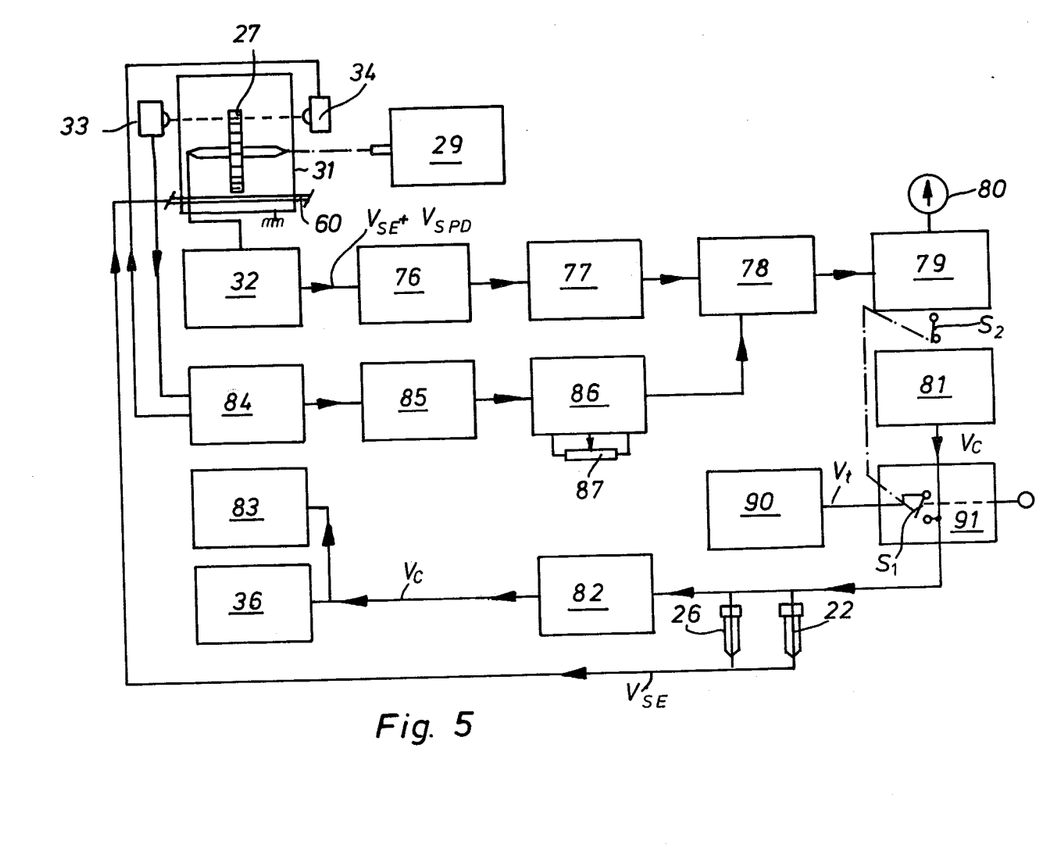
FIG. 5 is the electrical block circuit of the apparatus.

The electric block circuit of the apparatus is illustrated in FIG. 5 wherein the different blocks have the following functions. Block 32 is the pre-amplifier for the signal measured on the rotary electrode 27; block 76 is an active filter for selective transmission of signals at the measuring frequency, and for suppression of all the other disturbing frequencies caused by vibrations, electrical disturbances, etc. The measuring frequency is determined by the number of poles of the measuring electrode and the rotational velocity of the electrode. This frequency is preferably chosen such that it differs from the frequency of the main supply and its harmonics. Block 77 is an A.C. amplifier. The block 78 is a phase-sensitive rectifier, whereas block 79 is an amplifier for amplifying the signal that arises from the difference between $V_{se}+V_{spd}$ and $V_c$. This signal can be read on a measuring device 80 and it is moreover fed to an integrator 81. The integrator 81 integrates the output of 79, and goes on doing so until a signal $V_c$ has been produced that compensates $V_{se}+V_{spd}$, so that the reading at 80 has become zero.

Via a buffer circuit 82, the signal $V_c$ is fed to a voltage recorder 36, and may also displayed by a digital measuring device 83. A test voltage $V_t$ that is produced by a circuit 90, may be superimposed on the voltage of the measuring circuit by means of a switch circuit 91, in order to test the circuit and to adjust it for maximum sensitivity.

The output signal of the photocell 33 is processed as follows. The signal triggers a trigger circuit 84. Since the signal of the photocell 33 is not perfectly periodic because it is disturbed by mechanical vibrations, imperfections of the wheel construction, etc., the output signal of the trigger 84 is truly periodic. Therefore, this signal is passed through a stabiliser circuit 85 that comprises an active filter tuned to the measuring frequency, and a pulse shaper. The signal thus produced is amplified in an amplifier 86 which has a phase-corrector 87 whereby the phase of the output signal of the amplifier 86 that is used to control the phase-sensitive rectifier 78, may be shifted.

The operation of the apparatus is now described by way of example. The vessel 10 is filled with a predetermined amount of demineralized water. The temperature control circuit is set to the desired measuring temperature of the liquid. The capillary tube 16 is adjusted, while the cover 57 of the measuring chamber 31 is open, to a position such that the distance l (FIG. 2) between the outlet end of the tube and the mid-thickness plane of the measuring wheel, and the flow rate Q of the jet are related to the aging time t of the freshly formed liquid-/air interface of the jet leaving the tube 16, in accordance with the formula:

$$t=(K.\pi.d^2.l)/Q$$

wherein:
t is the ageing time in milliseconds,
K is a constant, equal to 15,
d is the diameter of the jet in mm,
l is the measuring distance in mm, and
Q is the pump flow rate in $ml.min^{-1}$.

The tube 16 is adjusted moreover in such a way that the jet is initially directed slightly upwardly so that as a consequence of its parabolic path, it is directed horizontally at the moment it passes the wheel 27. The adjustment is moreover preferably such that the point where the jet passes the measuring wheel is loated in a horizontal plane that contains the axis of rotation of the wheel. This plane has been indicated by the dot-dash line 92 in FIG. 3. Consequently the jet 60 may undergo minor deviations in a vertical plane, without causing a substantial alteration of the separation distance c between the electrode teeth (or poles) and the jet.

The final adjustment of the apparatus is the setting of the distance c (see FIG. 3) by means of the screw slide assembly 42 whereby the measuring chamber 31 can be moved bodily towards or away from the measuring wheel. The distance c is set at a value between about 0.2 and about 0.5 mm.

The cover 57 of the measuring chamber is then closed and the processing circuit 35 is switched on. The measuring instrument 80 shows initially a strong deflection, the rapidly returns towards a position that is close to the zero position. The block 91 is actuated by the operator so that the switch $S_1$ is closed and the switch $S_2$ is opened. By the closing of $S_1$ the test voltage $V_t$ of the circuit 90 is superimposed upon the voltage $V_c$, whereas the opening of $S_2$ prevents the compensation of the applied test voltage by the integrator. The test voltage $V_t$ causes the meter 80 to deflect again. Since the signal with the correct phase will have the greatest amplitude, it will be understood that adjustment of the phase controller 87 to obtain a maximum deflection of the meter 80 will result in the maximum measurement sensitivity of the apparatus. The circuit 91 is then actuated to remove the voltage $V_t$ from the line. Switch $S_2$ is now closed and $S_1$ opened, so that the voltage which appars on the digital voltmeter 83 is actually the algebraic sum of the contact potential of the standard electrodes, in the present case 243 mV for a calomel electrode at 20° C., and of the difference between the surface potential of the solution and the surface potential of the electrode.

An accurate amount of a solution of a determined concentration of one or more wetting agents is added to the contents of vessel 10 and the measuring device 83 is observed. As the added agents reach the electrode the reading starts to change and after about a further 10 seconds, the liquid becomes homogeneous and a steady reading is obtained. The difference between the second and the first reading indicates the surface potential difference that has been caused by the wetting agent(s)

under consideration, at the given concentration and temperature.

The obtained reading is indicative only for the particular ageing time. The operation may then be repeated for other aging times which may be obtained either by changing the flow rate Q of the pump 11 or by changing the distance l, or by changing both parameters, and a diagram may then be plotted showing the dynamic surface potential $V_{sp}$ caused by a given wetting agent as a function of the ageing time t of the liquid/air interface.

Figure 6:
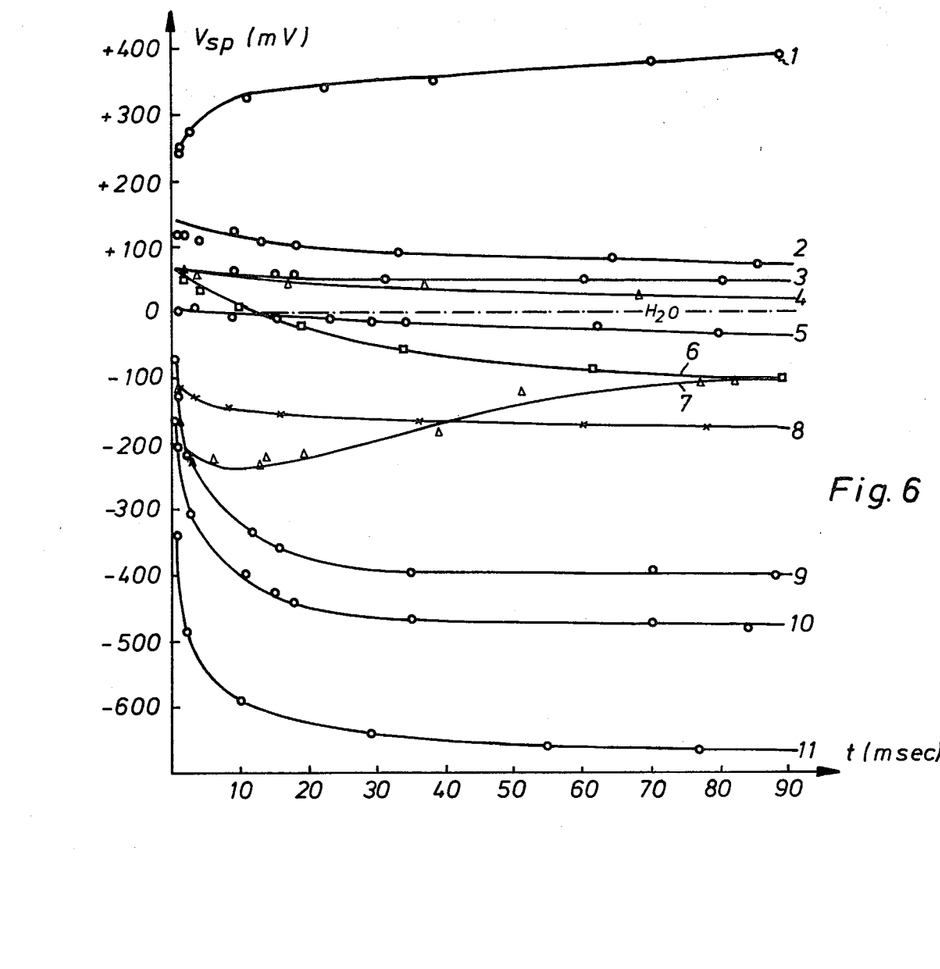
FIG. 6 is a diagram showing the surface adsorption as a function of time, of different wetting agents.

The diagram of FIG. 6 illustrates the surface adsorption values that have been obtained for different wetting agents that are commonly used in the coating of photographic layers. The measured results have been plotted in terms of the plus or minus difference between the measured dynamic surface potential (in millivolts) against the measured value for demineralized water. The values of the table are thus relative values. The time values on the abscissa are milliseconds. The different symbols indicate the respective measuring points that served for the construction of each curve. The different curves stand for the following solutions:

curve 1: a 5% active concentration of 10 ml per liter water at 22° C., of a wetting agent with the following formula: $C_7F_{15}COONH_4$ curve 2: a 4% active concentration of 10 ml per liter water at 22° C., of a wetting agent with the following formula: $nC_{16}H_{33}SO_3Na$ curve 3: a 1.4% active concentration of 40 ml per liter water at 22° C., of a wetting agent with the following formula: $i-C_{14}H_{29}OSO_3Na$ curve 4: a 1% active concentration of 50 ml per liter water at 22° C., of a wetting agent with the following formula: $NaSO_3-CH-COO-iC_8H_{17}CH_2-COO-iC_8H_{17}$ curve 5: a 11% active concentration of 5 ml per liter water at 22° C., of Saponine from Quillaja-bark curve 6: a 1.6% active concentration of 10 ml per liter water at 22° C., of a wetting agent with the following formula: $oleyl-CON(CH_3)-CH_2CH_2SO_3Na$ curve 7: a 5% active concentration of 10 ml per liter water at 22° C., of a wetting agent with the following formula: $C_7F_{15}CONH(CH_2CH_2O)_{17}H$ curve 8: a 1% concentration of gelatin in water at 30° C., curve 9: a 4.1% active concentration of 10 ml per liter water at 22° C., of a wetting agent with the following formula: $iC_8H_{17}-C_6H_4-O(CH_2CH_2O)_8CH_2COONa$ curve 10: a 5% active concentration of 10 ml per liter water at 22° C., of a wetting agent with the following formula: $iC_9H_{19}-C_6H_4-O(CH_2CH_2O)_{9.5}H$ curve 11: a 5% active concentration of 10 ml per liter water at 22° C., of the following wetting agent: $C_{12}C_{14}$ alkyl, benzyl, dimethyl ammonium chloride.

The following operation data, which relate to the apparatus described with reference to FIGS. 1 to 5, have been used with successful results.

Diameter of the jet: 1.5 mm
Rotary electrode:
  diameter 50 mm
  thickness 5 mm
  18 teeth
Revolutions per minute: 250
Measuring frequency: 75 Hz
Pump flow rate: 120 to 400 ml.min$^{-1}$
Measuring distance l: between 3.5 and 250 mm (no measurable variation of jet diameter)
aging (adsorption) times: between 0.9 and 160 ms
accuracy of measurement: 1 mV
stability: deviations smaller than 5 mV/h.

The minimum pump flow rate that could be used at the longest measuring distance (250 mm) while still maintaining a steady jet stream was 165 ml.min$^{-1}$.

The apparatus can be provided with a number of control circuits that are not required for the basic operation of the apparatus, but would improve the operability thereof. These controls included a circuit for suppressing the digital display at 36 in case the signal at 80 is too large, a circuit for signalling contamination of the measuring electrode such as may occur by touching by hand or by the jet liquid, and a circuit for signalling an unlocked measuring chamber, or a stationary measuring wheel.

As to the contamination of the measuring electrode, it was shown that the apparatus could be operated for hours without the occurrence of any disturbing condensation of vapours of the liquid that was being measured on the electrode.

It will be understood that the invention is not limited to the illustrated apparatus.

The rotary measuring electrode may have other forms than the illustrated one. For example the teeth may be shaped otherwise, the axis of rotation may be inclined to the horizontal, etc. The interruptions in the peripheral surface of the rotary electrode may be filled by a solid dielectric material rather than be open to the air. In that way disturbances of the air by the rotating wheel may be reduced. However great care must be taken in such case that no residual electric charges remain on the dielectric parts of the electrode which could thereby disturb the measurement.

The measuring chamber may be arranged for a forced air ventilation to avoid any possible condensation of liquid vapours on the measuring wheel. The risk of such condensation increases as the temperature of the liquid at which the measurement is carried out, increases.

The apparatus may be so arranged that the measuring chamber may be displaced along the jet according to a path that has a parabolic shape corresponding almost with that of the jet. In this way, an automatic recording of the adsorption behaviour of a wetting agent may be made over a desired aging range, by coupling the displacement of the chamber to the X-input of an XY-recorder, and the output signal of the apparatus to the Y-input of such recorder.

The method and apparatus according to the invention do not necessarily need a jet for the formation of a free surface of the solution to be examined. As mentioned already in the introduction of the specification, a channel apparatus can also be used to form a free surface. In that case the periphery of the rotary electrode should pass over the channel, the liquid stream passing just underneath the lowest point of the circular path of the electrode. The channel-forming means being necessarily constructed of non-conductive material, care should be taken to avoid the presence of residual electric charges in the vicinity of the channel for the liquid, that would cause erroneous indications of the actual dynamic surface potential of the solution.

We claim:

1. In a method of determining the dynamic surface potential of a solution, wherein the solution is formed into a steady steam having a free surface, and the difference between the surface potential of a reference electrode and the surface potential of the solution at a position along said stream is determined and used as a measure of said dynamic surface potential, the improvement comprising the steps of rotating an electrode having at least one electrically conductive peripheral surface portion thereon repeatedly in a direction across the path of the liquid stream to thereby generate a succession of potential difference signals, and determining the dynamic surface potential of the solution from said succession of signals.

2. A method according to claim 1, wherein the path of movement of the electrode periphery across the liquid stream is substantially normal to the direction of the stream at that point.

3. A method according to claim 1, wherein the surface of the solution stream and the electrode at its closest position to the stream are spaced apart less than 1 mm.

4. A method according to claim 1, wherein said stream is in the form of a jet.

5. A method according to claim 4, wherein the trajectory of the jet is substantially horizontal to the point crossed by the electrode path, and wherein the electrode is rotated about a horizontal axis which is in substantially the same horizontal plane as the axis of the jet at the measuring position.

6. Apparatus for determining the dynamic surface potential of a solution, comprising means for producing a steady stream of said solution, said stream having a free surface, an electrode mounted for rotation in an operative position adjacent said free surface at a locus along such stream for determining the difference between the surface potential of the solution at said locus and the surface potential of said electrode, said electrode having at least one electrically conductive surface portion on its periphery, and means for rotating said electrode to cause said surface portion to move repeatedly along a path across said stream, to thereby generate, for the determination of said potential difference, a plurality of potential difference signals.

7. Apparatus according to claim 6, wherein said rotary electrode is in the form of a metal disc or wheel with an interrupted peripheral surface.

8. Apparatus according to claim 6, wherein said electrode has a plurality of conductive surface portions spaced angularly around its periphery whereby a plurality of said potential difference signals are generated for each rotation of said electrode.

9. Apparatus according to claim 6, wherein said rotatable electrode is enclosed within an electrical shield chamber and is driven via a magnetic coupling from a power source located outside said chamber.

10. Apparatus according to claim 6, wherein the means for producing said stream comprises a capillary tube the bore of which is restricted at its outlet end by at least 15% whereby said stream is formed as a jet.

* * * * *